United States Patent

Kaplan et al.

[11] Patent Number: 5,123,912
[45] Date of Patent: Jun. 23, 1992

[54] ABSORBABLE COATING COMPOSITION, COATED SUTURES AND METHOD OF PREPARATION

[75] Inventors: Donald S. Kaplan, Weston; Ross R. Muth, Brookfield, both of Conn.

[73] Assignee: United States Surgical Corporation, Norwalk, Conn.

[21] Appl. No.: 707,437

[22] Filed: May 28, 1991

Related U.S. Application Data

[63] Continuation of Ser. No. 393,017, Aug. 10, 1989, abandoned, which is a continuation of Ser. No. 89,734, Aug. 26, 1987, abandoned.

[51] Int. Cl.$^5$ .............................................. A61L 17/00
[52] U.S. Cl. ..................... 606/230; 606/231; 427/2; 428/275; 528/354
[58] Field of Search ............. 427/2; 428/275; 528/354, 408; 606/230, 231

[56] References Cited

U.S. PATENT DOCUMENTS

| | | | |
|---|---|---|---|
| 2,917,410 | 12/1959 | Vitalis | 428/272 |
| 3,531,561 | 9/1970 | Trehu | 128/335.5 |
| 3,942,532 | 3/1976 | Hunter et al. | 128/335.5 |
| 4,027,676 | 6/1977 | Mattei | 128/335.5 |
| 4,043,344 | 8/1977 | Landi et al. | 128/335.5 |
| 4,047,533 | 9/1977 | Perciaccante et al. | 128/335.5 |
| 4,080,969 | 3/1978 | Casey et al. | 128/335.5 |
| 4,452,973 | 6/1984 | Casey et al. | 528/354 |
| 4,523,591 | 6/1985 | Kaplan et al. | 128/334 R |
| 4,716,203 | 12/1987 | Casey et al. | 128/335.5 |
| 4,857,602 | 8/1989 | Casey et al. | 606/231 |

FOREIGN PATENT DOCUMENTS 1332505 10/1973 United Kingdom ............. 128/335.5

Primary Examiner—Randall L. Green
Assistant Examiner—Paul Prebilic
Attorney, Agent, or Firm—Thomas R. Bremer; Peter G. Dilworth; Rocco S. Barrese

[57] ABSTRACT

An absorbable coating composition useful for coating sutures, said absorbable coating composition comprising a copolymer derived from (i) the copolymerization of a polyalkylene glycol, glycolide monomer and lactide monomer or (ii) the copolymerization of a polyalkylene glycol and a copolymer of lactide and glycolide and multifilament sutures coated with same.

19 Claims, No Drawings

ABSORBABLE COATING COMPOSITION, COATED SUTURES AND METHOD OF PREPARATION

This is a continuation of application Ser. No. 07/393,017 filed on Aug. 10, 1989, now abandoned which is a continuation of Ser. No. 07/089,734 filed on Aug. 16, 1987, now abandoned.

BACKGROUND OF THE INVENTION

This invention relates to an absorbable coating composition for surgical sutures and more particularly to coated, surgical sutures having, among other desirable characteristics, improved knot tie-down properties.

Monofilament synthetic absorbable suture materials are generally stiffer than their catgut or collagen counterparts and therefore synthetic absorbable sutures are usually employed in a multifilament, such as a braided or twisted construction, in order to provide the suture with the desired degree of softness and flexibility. Multifilament sutures, however, exhibit a certain degree of undesirable roughness, in what is generally referred to as tie-down performance, i.e. the ease or difficulty of sliding a knot into place down the suture.

Thus, the problem of improving knot tie-down performance of multifilament surgical sutures has been the subject of considerable research. For example, U.S. Pat. No. 4,027,676 relates to an absorbable coated multifilament suture disclosed to have improved tie-down properties. In particular, the absorbable coated suture of this patent consists of a synthetic absorbable suture coated with an absorbable composition consisting of an absorbable film-former, an absorbable lubricant and an absorbable hydrophobic material. Suitable film formers according to this patent include homopolymers of lactide and glycolide, i.e. polylactide, polyglycolide and copolymers of lactide and glycolide with each other and with other reactive monomers, copolymers of vinyl acetate with unsaturated carboxylic acids such as crotonic, acrylic and methacrylic acids; water soluble or dispersible cellulose derivatives such as methyl cellulose, hydroxymethyl cellulose and carboxymethyl cellulose; natural gums; high molecular weight crystalline ethylene oxide polymers; polyacrylamide; collagen; gelatin; polyamino acids; polyvinyl alcohol; polyvinyl pyrrolidone and absorbable conjugated unsaturated triglycerides, such as dehydrated castor oil. The lubricant of the composition is disclosed to be a polyethylene glycol having a molecular weight of less than about 200,000, such as copolymers of ethylene oxide and propylene oxide. Particularly preferred is polyethylene glycol at a molecular weight of from about 4,000 to about 200,000 and more preferably from 5000 to 50,000. The hydrophobic material is disclosed as a higher fatty acid having more than about 12 carbon atoms such as stearic acid or an ester of such a fatty acid such as sorbitan tristearate and hydrogenated castor oil.

Similarly, U.S. Pat. Nos. 4,043,344 and 4,047,533 disclose that the handling characteristics, particularly knot run down and tissue drag of non-absorbable and absorbable sutures can be improved by a coating of a lubricating film of a bioabsorbable copolymer having polyoxyethylene blocks and polyoxypropylene blocks, e.g. Pluronics.

U.S. Pat. No. 3,942,532 discloses that the tie-down performance of braided sutures may be improved by coating the surface with a polyester derived from the polymerization of lactones as a polyester obtained by esterifying low molecular weight glycols with a dimeric acid.

U.S. Pat. No. 4,080,969 discloses improved knot tie down properties may be imparted to a suture by coating the suture with a hydrolyzable polyester resin of a diglycolic acid and an unhindered glycol, such as ethylene glycol or diethylene glycol.

Numerous other patents disclose sutures and/or coated sutures having improved handling characteristics. These include, U.S. Pat. No. 4,452,973, U.S. Pat. No. 4,201,216, U.S. Pat. No. 4,224,946, U.S. Pat. No. 4,314,561, U.S. Pat. No. 4,105,034, U.S. Pat. No. 4,185,637, U.S. Pat. No. 4,532,929, U.S. Pat. No. 4,608,428, U.S. Pat. No. 3,867,190, U.S. Pat. No. 3,540,452, U.S. Pat. No. 3,527,650, U.S. Pat. No. 3,379,552 and U.S. Pat. No. 3,655,927, among others.

Notwithstanding the extensive research in attempting to improve the tie-down characteristics of surgical sutures, sutures having even further improved knot tie-down properties are still desirable.

SUMMARY OF THE INVENTION

Accordingly, it is one object of the present invention to provide an absorbable coating composition for surgical sutures, particularly multifilament synthetic sutures.

Another object of this invention is to provide a coated surgical suture having improved knot tie down properties.

Still another object of the present invention is to provide an absorbable, coated synthetic suture having improved knot tie-down properties under both wet and dry conditions.

A further object of this invention is to provide an absorbable, coated synthetic suture having an improved coated which is not readily susceptible to wash off under wet conditions.

A still further object of the present invention is to provide a method for imparting improved knot tie-down properties to synthetic absorbable multifilament sutures.

These and other objects are achieved herein by providing an absorbable polymeric coating composition comprising either (i) a copolymer derived from the copolymerization of a low molecular weight polyalkylene glycol, a glycolide monomer and a lactide monomer or (ii) a copolymer derived from the copolymerization of a low molecular weight polyalkylene glycol and a preformed copolymer of lactide and glycolide. Coated sutures, having improved knot tie-down properties, under dry and wet conditions, are provided by depositing a coating of the afore-described coating composition on the suture.

DETAILED DESCRIPTION OF THE INVENTION

It has been discovered herein that the knot tie-down characteristics of multifilament sutures, such as braided or twisted sutures, are improved by applying a surface coating of a non-toxic, physiologically inert absorbable coating composition derived from the (i) copolymerization of a low molecular weight polyalkylene glycol with small quantities of glycolide monomer and L-lactide monomer or (ii) the copolymerization of low molecular weight polyalkylene glycol with a copolymer of lactide and glycolide.

Suitable low molecular weight polyalkylene glycols useful in the practice of the present invention include those, for example, having the general formula:

$$HO\text{-}[RO]_y\text{-}H$$

wherein R is alkylene having from 2-4 carbon atoms, preferably 2 carbon atoms, and y is an integer from about 100 to about 350, preferably from about 100 to about 250. Thus, suitable molecular weights for the polyalkylene glycols of the present invention range from about 3500 to about 25,000 and preferably from about 4,000 to about 10,000.

In preparing the coating compositions of the present invention, the afore-described polyalkylene glycol is copolymerized with small amounts of glycolide monomer and L-lactide monomer in the presence of a suitable catalyst. In another embodiment of the present invention, the coating composition is prepared by copolymerizing the polyalkylene glycol polymer with a preformed copolymer of lactide and glycolide. Suitable copolymerization catalysts for both of these copolymerization processes, include stannous chloride, stannous octoate and the like. It should be understood, however, that the copolymerization scheme employing a pre-made copolymer may be carried out with or without a copolymerization catalyst.

In the copolymerization process wherein glycolide monomer and lactide monomer are employed, suitable amounts of glycolide monomer include from about 10% to about 35%, by weight, based on total weight of glycolide and lactide monomers, while suitable amounts of lactide monomer include from about 90 to about 65% by weight, based on total weight of glycolide and lactide monomers. In the copolymerization process employing the preformed copolymer of lactide and glycolide, the preformed copolymer generally comprises from about 10 to about 35 mole %, glycolide and 90 to about 65 mole %, lactide. The preferred preformed copolymer composition is comprised of 18 mole % glycolide and 82 mole % lactide. Suitable preformed copolymers of glycolide and lactide which are used in the practice of the present invention and their method of preparation are described in U.S. Pat. No. 4,523,591, the entire contents of which are incorporated herein by reference.

In general, however and notwithstanding the utilization of glycolide and lactide monomer or preformed lactide/glycolide copolymer in the preparation of the coating compositions of the present invention, the weight ratio of polyalkylene glycol to combined lactide and glycolide monomer or lactide/glycolide copolymer utilized in the copolymerization process is from about 4:1 to about 1:4, preferably 2:1 to about 1:2, respectively. Typically, copolymerization is carried out in an inert atmosphere, e.g., nitrogen, at temperatures, for example, of from about 125°–200° C., preferably 150° C. to about 160° C., for a period of from about 10 to about 24 hours.

The absorbable, coating compositions of the present invention are non-toxic and physiologically inert and are applied to the multifilament suture surface as a solution and/or dispersion of the polymeric coating composition in a volatile solvent, such as methylene chloride or acetone. Solidification of the coating on the suture surface is accomplished by volatilizing the solvent.

The coating composition may be applied to the multifilament suture by any suitable process, such as passing the suture through a solution of the coating composition or past a brush or applicator melted with the solution or past one or more spray nozzles dispensing the solution as droplets. The suture wetted with the coating solution is subsequently passed through or held in a drying oven for a time and at a temperature sufficient to volatilize the solvent.

The coating composition may, if desired, also contain components other than those discussed above for other purposes such as, for example, dyes, antibiotics, antiseptics, anesthetics, anti-inflammatory agents.

The amount of coating composition applied to the suture, will vary depending upon the construction of the suture, e.g., the number of filaments, tightness of braid or twist, and the size of the suture and the composition thereof. In general, the coating composition applied to an "unfilled" (i.e. not containing a storage stabilizing agent) braided suture will constitute from about 1.0 to about 3.0 percent by weight of the coated suture, but the amount of coating add on may range from as little as about 0.5 percent, by weight, to as much as 4.0 percent or higher. For a preferred "filled" (i.e. containing a storage stabilizing agent) braided suture, amounts of coating composition generally comprise from about 0.5% to 2.0% with as little as 0.2% to as much as 3.0%. As a practical matter and for reasons of economy and general performance, it is generally preferred to apply the minimum amount of polymeric coating composition of the present invention consistent with good tie-down performance and this level of coating add on is readily determined experimentally for any particular suture-coating system.

Preferred filled sutures, such as glycerin filled braided sutures, which can be coated in accordance with the present invention, are described in commonly assigned, copending U.S. patent application filed concurrently herewith, the entire contents of which are incorporated herein by reference. As disclosed in said copending U.S. application, in addition to glycerin and its mono- and diesters derived from low molecular weight carboxylic acids, e.g. monoacetin and diacetin, other water soluble hygroscopic polyhydroxy compounds or esters thereof which are useful in these "filled" sutures include ethylene glycol, diethylene glycol, triethylene glycol, 1,3-propanediol, trimethylolethane, trimethylolpropane, pentaerythritol, sorbitol, and the like. Glycerin, however, is especially preferred. Mixtures of these storage stabilizing agents, e.g., sorbitol dissolved in glycerin, glycerin combined with monoacetin and/or diacetin, etc., are also useful.

In the preparation of a filled suture which is suitable to be coated with the absorbable polymeric coating composition of the present invention, application of the storage stabilizing agent to the suture can be carried out in any number of ways. Thus, for example, the suture can be submerged in the storage stabilizing agent or solution thereof until at least a storage stabilizing amount of agent is acquired or otherwise retained by the suture. In many cases, contact times on the order of from just a few seconds, e.g., about 10 seconds or so, to several hours, e.g., about 2 hours and even longer, are sufficient to impart a substantial improvement in the storage stability of the suture.

The foregoing submersion method of contacting the suture with storage stabilizing agent can be conducted continuously or in batch. Thus, in the case of an absorbable suture, a running length of the suture can be continuously passed through a quantity of the stabilizing agent at a velocity which has been previously determined to provide the necessary degree of exposure, or contact time, of the suture with the storage stabilizing agent. As the suture emerges from the storage stabilizing agent, it can be passed through a wiper or similar device to remove excess agent prior to the packaging operation. In a batch operation, a quantity of suture is merely submerged within the storage stabilizing agent for the requisite period of time with any excess agent being removed from the suture if desired.

Alternatively, the storage stabilizing agent can be applied by spraying, brushing, wiping, etc., on the surfaces of the suture such that the latter receive and retain at least a storage stabilizing amount of the agent. Yet another procedure which can be used to apply the storage stabilizing agent involves inserting the suture in a package containing an effective amount of the agent such that intimate contact between the suture and the agent will be achieved.

Whatever the contacting procedure employed, it is necessary that the article being treated acquire a storage stabilizing amount of the storage stabilizing agent. In general amounts of from about 2 to about 25, and preferably from about 5 to about 15 weight percent, of storage stabilizing agent(s) (exclusive of any solvent) by weight of the suture contacted therewith is sufficient to provide significantly improved storage stability.

The term "filled" as used herein refers to the association of the suture with a storage stabilizing amount of storage stabilizing agent whether this association be one in which the storage stabilizing agent is absorbed by the suture, is present on the surface thereof or is a combination of the two.

The polymeric coating composition of the present invention may be applied to any suture material where it is desired to improve fiber lubricity, suture tie-down characteristics or the like. The coating compositions of the present invention are particularly useful with synthetic, absorbable multifilament sutures, braided or unbraided, comprised of, for example, polylactide, polyglycolide, copolymers of lactide and glycolide, poly(p-dioxanone) and mixtures of such polymers with each other and other compatible absorbable compositions. Particularly preferred absorbable, multifilament sutures for the purposes of the present invention are comprised of copolymers of lactide and glycolide, said copolymers, for example, being disclosed in U.S. Pat. No. 4,523,591, the entire contents of which are incorporated herein by reference. Moreover, as described hereinbefore, absorbable, braided sutures filled with glycerin or other water soluble hygroscopic polyhydroxy compound, in amounts of from about 2 to about 25%, are also preferred herein. In addition to stabilizing the suture, the glycerin filling improves the handleability of the coated suture as well as allows lower levels of coating to be applied to the suture. As stated hereinbefore, these filled sutures are described in commonly assigned, copending concurrently filed U.S. patent application, the entire contents of which are incorporated herein by reference.

Non-absorbable sutures are also contemplated within the scope of the present invention. Typically these include braided or unbraided silk, cotton, nylon, polyester, polypropylene, polyethylene and linen sutures.

To measure improvement of tie down properties imparted to sutures, for example, synthetic absorbable sutures, in a quantitative fashion, an Instron tensile tester is used to simulate knot slide down and the resistance a surgeon might experience.

Suture tie down properties are evaluated dry after the sutures are conditioned for at least 24 hours in vacuum at room temperature, and wet after being immersed in water at 37° C. for 1 minute.

A suture sample is tested for knot run down performance using the following method. The suture to be tested is cut to approximately 30 cm. lengths. A length of suture is wrapped once around a 2.5 cm diameter tube and tied in a simple sliding one over one knot (square knot) and snugged down on the tube. The suture is then removed from the tube and the ends of the suture are clamped in 1 inch square rubber coated flat grips mounted on an Instron Model 1011 Tensile tester. The Instron is equipped with a 5 kg load transducer with load range set at 5000 grams and crosshead speed 10–50 mm/min.

As the suture passes over itself, a curve is plotted on the graph paper. Since a braided suture has braid protrusions and is somewhat elliptical in cross section, a smooth curve does not appear. The "stick" portion of the stick-slip curve is produced when it is easier for the suture to stick to itself and elongate than to slip. As the suture is elongated more and more, the tension continues to build-up until either the yield point of the suture is reached or until the cohesive force is overcome and the suture knot slips. This cycle is repeated producing a saw tooth pattern on the chart, the magnitude of which gives a measure of braid "chatter" or the smoothness of tie down.

The surface lubricity of the suture may be determined from the maximum and minimum friction peaks on the graph in accordance with the following equation:

$$\text{average lubricity} = \text{minimum peak} + \frac{(\text{maximum peak} - \text{minimum peak})}{2}$$

In order that those skilled in the art may better understand how the present invention may be practiced, the following examples are given by way of illustration and not by way of limitation.

EXAMPLE 1

Fifty (50) grams of polyethylene glycol (MW 7500, available from BASF) was placed in a 250 ml. three necked flask equipped with a stirrer and inlet/outlet nitrogen gas lines. The polyethylene glycol in the flask is stirred and heated at about 150° C. for about 3 hours while maintaining a low level dry nitrogen purge. After 3 hours, 0.02 grams of stannous chloride catalyst is added and stirring is increased to homogenize the catalyst/block copolymer mixture. A dry mixture of 83.2 grams of L-lactide and 16.8 grams of glycolide is added to the catalyst/block copolymer mixture in the flask under increased stirring conditions to dissolve the monomer. After polymerization is allowed to proceed for about 24 hours, the resultant polymer is allowed to cool to about 100° C. at which time about 75 ml. methylene chloride is added in two portions 50 ml. then 25 ml and stirred until homogeneous. The resultant solution is then poured into a clean dry crystallizing dish. The mixture is allowed to evaporate until solidified (about 24 hours). The solid polymer is placed in a vacuum over for three days (the first day at 80° C. for 24 hours, second day at 100° C. for 24 hours, third day at 120° C. for 24 hours) after which time the product is allowed to cool to room temperature and then removed from the oven. NMR Analysis of the product identifies it to be a copolymer of about 75 wt.% polyethylene oxide with 25 wt.% glycolide/lactide wherein the glycolide/lactide is in a 58:42 weight ratio, respectively.

A braided suture comprised of filaments of a glycolide/lactide copolymer containing 90% glycolide units was prepared for coating by soaking in glycerin/methanol solution. Methanol is dried from the braid under vacuum leaving glycerin (about 10% by weight) in the braid. The polymeric coating composition prepared above was dissolved in methylene chloride. The solution was pumped to a capillary to form a droplet. The filled braid was drawn through the droplet wetting the braid. The coating apparatus was a standard lab coater. The braid was dried in vacuum to remove methylene chloride. The knot tie down characteristics of the filled braided suture after coating are summarized in Table 1.

An unfilled (i.e. not soaked in glycerin) braided suture comprised of filaments of a glycolide/lactide copolymer containing 90% glycolide units was also coated with the polymeric coating composition prepared above dissolved in methylene chloride. The solution was pumped to a capillary to form a droplet. The braid was drawn through the droplet wetting the braid. The coating apparatus was a standard lab coater. The braid was dried in vacuum to remove methylene chloride. The knot tie down characteristics of the unfilled braided suture after coating are summarized in Table 1.

EXAMPLE 2

Fifty (50) grams of polyethylene glycol, (MW 7500 available from Polysciences) and 25 grams of a preformed glycolide/lactide copolymer comprised of (18 mole % glycolide and 82 mole % lactide units) are placed in a dry 3 neck flask. The flask and contents are heated in a vacuum oven to about 100° C. and maintained at that temperature for about 24 hours. The oven is then allowed to cool to room temperature and the vacuum broken with dry nitrogen only. The flask and contents are again heated under nitrogen purge to about 160° C. After the mass in the flask has melted, slow stirring is commenced. When the mass is completely melted, 0.02 gram of stannous chloride catalyst is added under rapid stirring for about one minute to evenly disperse the catalyst. Slow stirring is continued for about 47 hours after which the mass is allowed to cool. 75 ml. in two portions: 50 ml., then 25 ml. of methylene chloride are added to the mass and stirred until homogeneous. The solution is then poured into a crystallizing dry dish and allowed to stand until all the methylene chloride has evaporated and the polymer has solidified. Post-treatment of the polymer is carried out as in Example 1. The copolymer product is made in virtually 100% conversion. NMR Analysis of the product identifies it to be a copolymer consisting of polyethylene glycol and glycolide/lactide blocks with virtually the same ratio in the finished product as in starting material.

A braided suture comprised of filaments of a glycolide/lactide copolymer containing 90% glycolide units was prepared for coating by soaking in glycerin/methanol solution. Methanol is dried from the braid under vacuum leaving glycerin (about 10% by weight) in the braid. The polymeric coating composition prepared above was dissolved in methylene chloride. The solution was pumped to a capillary to form a droplet. The filled braid was drawn through the droplet wetting the braid. The coating apparatus was a standard lab coater. The braid was dried in vacuum to remove methylene chloride. Approximately 1.1% coating by weight was added to the braid. The characteristics of the filled braided suture after coating are summarized in Table 1.

An unfilled braided suture comprised of filaments of a glycolide/lactide copolymer containing 90% glycolide units was also coated with the polymeric coating composition prepared above dissolved in methylene chloride. The solution was pumped to a capillary to form a droplet. The braid was drawn through the droplet wetting the braid. The coating apparatus was a standard lab coater. The braid was dried in vacuum to remove methylene chloride. The knot tie-down characteristics of the braided suture after coating are summarized in Table 1.

EXAMPLE 3

Fifty (50) grams of polyethylene glycol (MW 7500, available from Polysciences) and 25 grams of a preformed glycolide/lactide copolymer comprised of 18 mole % glycolide and 82 mole % lactide units are placed in a dry 3 neck flask. The flask and contents are heated in a vacuum oven to about 100° C. and maintained at that temperature for abut 24 hours. The oven is then allowed to cool to room temperature and the vacuum broken with dry nitrogen only. The flask and contents are again heated under nitrogen purge to about 160° C. After the mass in the flask has melted, slow stirring is commenced. When the mass is completely melted, 0.02 gram of stannous chloride catalyst is added under rapid stirring for about one minute to evenly disperse the catalyst. Slow stirring is continued for about 24 hours after which the mass is allowed to cool. 75 ml. in two portions: 50 ml. then 25 ml. of methylene chloride are added to the mass and stirred until homogeneous. The solution is then poured into a crystallizing dry dish and allowed to stand until all the methylene chloride has solidified. Post-treatment of the polymer is carried out as in Example 1. NMR Analysis of the product identifies it to be a copolymer consisting of polyethylene glycol and glycolide/lactide blocks with virtually the same ratio in finished product as in starting material.

A braided suture comprised of filaments of a glycolide/lactide copolymer containing 90% glycolide units was prepared for coating by soaking in glycerin/methanol solution. Methanol is dried from the braid under vacuum leaving glycerol (about 10% by weight) in the braid. The polymeric coating composition prepared above was dissolved in methylene chloride. The solution was pumped to a capillary to form a droplet. The filled braid was drawn through the droplet wetting the braid. The coating apparatus was a standard lab coater. The braid was dried in vacuum to remove methylene chloride. Approximately 1.6% coating by weight was added to the braid. The characteristics of the filled braided suture after coating are summarized in Table 1.

An unfilled braided suture comprised of filaments of a glycolide/lactide copolymer containing 90% glycolide units was also coated with the polymeric coating composition prepared above dissolved in methylene chloride. The solution was pumped to a capillary to form a droplet. The braid was drawn through the droplet wetting the braid. The coating apparatus was a standard lab coater. The braid was dried in vacuum to remove methylene chloride. The knot tie down characteristics of the braided suture after coating are summarized in Table 1.

EXAMPLE 4

Fifty (50) grams of polyethylene glycol (MW 7500 available from Polysciences) and 25 grams of a preformed glycolide/lactide copolymer comprised of 18 mole % glycolide and 82 mole % lactide units are placed in a dry 3 neck flask. The flask and contents are heated in a vacuum oven to about 100° C. and maintained at that temperature for abut 24 hours. The oven is then allowed to cool to room temperature and the vacuum broken with dry nitrogen only. The flask and contents are again heated under nitrogen purge to about 160° C. After the mass in the flask has melted, slow stirring is commenced. Slow stirring is continued for about 24 hours after which the mass is allowed to cool. 75 ml. in two portions: 50 ml. then 25 ml. of methylene chloride are added to the mass and stirred until homogeneous. The solution is then poured into a crystallizing dry dish and allowed to stand until all the methylene chloride has solidified. Post-treatment of the polymer is carried out as in Example 1. NMR analysis of the product identifies it to be a copolymer consisting of polyethylene glycol and glycolide/lactide blocks with virtually the same ratio in finished product as in starting material.

A braided suture comprised of filaments of a glycolide/lactide copolymer containing 90% glycolide units was prepared for coating by soaking in glycerin/methanol solution. Methanol is dried from the braid under vacuum leaving glycerol (about 10% by weight) in the braid. The polymeric coating composition prepared above was dissolved in methylene chloride. The solution was pumped to a capillary to form a droplet. The filled braid was drawn through the droplet wetting the braid. The coating apparatus was a standard lab coater. The braid was dried in vacuum to remove methylene chloride. The physical characteristics of the filled braided suture before and after coating are summarized in Table 1.

An unfilled, braided suture comprised of filaments of a glycolide/lactide copolymer containing 90% glycolide units was also coated with the polymeric coating composition prepared above dissolved in methylene chloride. The solution was pumped to a capillary to form a droplet. The braid was drawn through the droplet wetting the braid. The coating apparatus was a standard lab coater. The braid was dried in vacuum to remove methylene chloride. The knot tie down characteristics of the braided suture after coating are summarized in Table 1.

EXAMPLE 5

37.5 grams of polyethylene glycol (MW 7500, available from Polysciences) and 37.5 grams of a preformed glycolide/lactide copolymer comprised of 18 mole % glycolide and 82 mole % lactide units are placed in a dry 3 neck flask. The flask and contents are heated in a vacuum oven to about 100° C. and maintained at that temperature for about 24 hours. The oven is then allowed to cool to room temperature and the vacuum broken with dry nitrogen only. The flask and contents are again heated under nitrogen purge to about 160° C. After the mass in the flask has melted, slow stirring is commenced. When the mass is completely melted, 0.02 gram of stannous chloride catalyst is added under rapid stirring to evenly disperse the catalyst for about one minute. Slow stirring is continued for about 24 hours after which the mass is allowed to cool. 75 ml. in two portions: 50 ml. then 25 ml. of methylene chloride are added to the mass and stirred until homogeneous. The solution is then poured into a crystallizing dry dish and allowed to stand until all the methylene chloride has evaporated and the polymer has solidified. Post-treatment of the polymer is carried out as in Example 1.

A braided suture comprised of filaments of a glycolide/lactide copolymer containing 90% glycolide units was prepared for coating by soaking in glycerin/methanol solution. Methanol is dried from the braid under vacuum leaving glycerin (about 10% by weight) in the braid. The polymeric coating composition prepared above was dissolved in methylene chloride. The solution was pumped to a capillary to form a droplet. The filled braid was drawn through the droplet wetting the braid. The coating apparatus was a standard lab coater. The braid was dried in vacuum to remove methylene chloride. The physical characteristics of the filled braided suture before and after coating are summarized in Table 1.

An unfilled braided suture comprised of filaments of a glycolide/lactide copolymer containing 90% glycolide units was also coated with the polymeric coating composition prepared above dissolved in methylene chloride. The solution was pumped to a capillary to form a droplet. The braid was drawn through the droplet wetting the braid. The coating apparatus was a standard lab coater. The braid was dried in vacuum to remove methylene chloride. The knot tie down characteristics of the braided suture after coating are summarized in Table 1.

EXAMPLE 6

25 grams of polyethylene glycol (MW 7500, available from Polysciences) and 50 grams of a preformed glycolide/lactide copolymer comprised of 18 mole % glycolide and 82 mole % lactide units are placed in a dry 3 neck flask. The flask and contents are heated in a vacuum oven to about 100° C. and maintained at that temperature for about 24 hours. The oven is then allowed to cool to room temperature and the vacuum broken with dry nitrogen only. The flask and contents are again heated under nitrogen purge to about 160° C. After the mass in the flask has melted, slow stirring is commenced. When the mass is completely melted, 0.02 gram of stannous chloride catalyst is added under rapid stirring to evenly disperse the catalyst for about one minute. Slow stirring is continued for about 24 hours after which the mass is allowed to cool. 75 ml. in two portions: 50 ml. then 25 ml. of methylene chloride are added to the mass and stirred until homogeneous. The solution is then poured into a crystallizing dry dish and allowed to stand until all the methylene chloride has evaporated and the polymer has solidified. Post-treatment of the polymer is carried out as in Example 1. NMR analysis of the product identifies it to be a copolymer consisting of polyethylene glycol and glycolide/lactide blocks with virtually the same ratio in the finished product as in the starting materials.

A braided suture comprised of filaments of a glycolide/lactide copolymer containing 90% glycolide units was prepared for coating by soaking in glycerin/methanol solution. Methanol is dried from the braid under vacuum leaving glycerin (about 10% by weight) in the braid. The polymeric coating composition prepared above was dissolved in methylene chloride. The solution was pumped to a capillary to form a droplet. The filled braid was drawn through the droplet wetting the braid. The coating apparatus was a standard lab coater.

The braid was dried in vacuum to remove methylene chloride. The characteristics of the filled braided suture after coating are summarized in Table 1.

An unfilled, braided suture comprised of filaments of a glycolide/lactide copolymer containing 90% glycolide units was also cited with the polymer coating composition prepared above dissolved in methylene chloride. The solution was pumped to a capillary to form a droplet. The braid was drawn through the droplet wetting the braid. The coating apparatus was a standard lab coater. The braid was dried in vacuum to remove methylene chloride. The knot tie down characteristics of the braided suture after coating are summarized in Table 1.

COMPARATIVE EXAMPLE 7

To demonstrate the superior results obtained by the copolymerized coating composition of the present invention, a non-copolymerized admixture was prepared for testing. That is, two parts, by weight polyethylene glycol (MW 7500, from Polysciences) and one part by weight preformed copolymer (20 mole % glycolide and 80 mole % lactide units) were dissolved in methylene chloride. This admixture was applied to unfilled braided sutures comprised of filaments of glycolide/lactide copolymer containing 90% glycolide units using a lab coater in similar conditions to those described in the previous examples. After initial stretching and tightening of the knot, the samples broke at the knot as shown by the data in Table 1.

about 65-90 mole percent lactide and from about 10-35 mole percent glycolide.

2. The absorbable coating composition of claim 1 wherein said polyalkylene glycol has the general formula:

wherein R is alkylene from 2 to 4 carbon atoms and y is an integer from about 100 to about 350.

3. The absorbable coating composition of claim 1 wherein the polyalkylene glycol is polyethylene glycol.

4. A suture having improved dry and wet knot tie-down properties, said suture being coated with an absorbable polymeric composition derived from the copolymerization of a polyalkylene glycol and a preformed copolymer of L-lactide and glycolide, wherein the weight ratio of polyalkylene glycol to preformed copolymer of L-lactide and glycolide employed in the copolymerization is from about 2:1 to about 1:2, respectively and wherein said preformed copolymer of L-lactide and glycolide consists essentially of from about 65-90 mole percent lactide and from about 10-35 mole percent glycolide.

5. The coated suture of claim 4 wherein the suture is a synthetic, absorbable, multifilament suture.

6. The coated suture of claim 5 wherein the synthetic, absorbable, multifilament suture is comprised of homopolymers or copolymers of lactide and glycolide.

TABLE 1

| Example | Weight polyethylene glycol (grams) | Weight glycolide (grams) | Weight lactide (grams) | glycolide/ lactide copolymer (grams) | % by weight coating on suture | Knot Run Down[1] (Avg.) Instron (Dry) (grams) | Knot Run Down (Avg.) Instron (Wet) (grams) |
| --- | --- | --- | --- | --- | --- | --- | --- |
| 1 | 50 | 16.8 | 83.2 | — | 2.1(U); 0.6(F)[2] | 200 | |
| 2 | 50 | — | — | 25 | 1.1(U); <1.5(F) | 50–500(F); 250(U) | 500–1000(F) 500–1000(U) |
| 3 | 50 | — | — | 25 | 1.6(U); <1.5(F) | 100–200(F) 200–400(U) | 500–1500(F) 500–1000(U) |
| 4 | 50 | — | — | 25 | 1.1(U); <1.0(F) | 100–200(F) 250–500(U) | 200–2000(F) 1000–3000(U) |
| 5 | 37.5 | — | — | 37.5 | 1.5(U); 1.0(F) | 150(F) 400–1000(U) | <1000(F) 1000–2000(U) |
| 6 | 25 | — | — | 50 | 2.9(U); 1.6(F) | 400–1000(F) 1000(U) | 1000–3000(F) 500–1500(U) |
| Comparative 7 | 50 | | | 25 | 1–1.5% | Broke at knot with no run-down at 4000–4300 grams | |

[1]All sutures size 1/0. Uncoated sutures break without knot run-down at approximately 4000–4300 grams.
[2]In this table (U) refers to sutures not prepared for coating by contact with glycerin; (F) refers to sutures with the glycerin pretreatment.

The above data show the improved knot tie down properties achieved by the absorbable polymeric coating compositions provided by the present invention.

Obviously, other modifications and variations of the present invention are possible in light of the above teachings. It is, therefore, to be understood that changes may be made in the particular embodiments of this invention which are within the full intended scope of the invention as defined by the appended claims.

We claim:

1. An absorbable coating composition useful for coating sutures, said absorbable coating composition comprising a copolymer derived from the copolymerization of a mixture of polyalkylene glycol and a preformed copolymer of L-lactide and glycolide, wherein the weight ratio of polyalkylene glycol to preformed copolymer of L-lactide and glycolide monomer employed in the copolymerization is from about 2:1 to about 1:2, respectively and wherein said preformed copolymer of L-lactide and glycolide consists essentially of from 7. The coated suture of claim 5 wherein the synthetic, absorbable, multifilament suture is a braided suture.

8. The coated suture of claim 7 wherein the braided synthetic, absorbable, multifilament suture is comprised of a copolymer of lactide and glycolide derived from about 65-90 mole percent lactide and from about 10-35 mole percent glycolide.

9. The coated suture of claim 4 wherein said suture is filled with water soluble hygroscopic polyhydroxy compound.

10. The coated suture of claim 9 wherein said water soluble hygroscopic polyhydroxy compound is glycerin.

11. The coated suture of claim 9 wherein said suture is filled with from about 2 to about 25% of glycerin, based on the weight of the suture.

12. The coated suture of claim 7 wherein said braided suture is filled with a water soluble hygroscopic polyhydroxy compound.

13. The coated suture of claim 12 wherein said water soluble hygroscopic polyhydroxy compound is glycerin.

14. A method of imparting dry and wet knot tie-down properties to a suture, said method comprising coating said suture with an absorbable, polymeric composition derived from the copolymerization of a polyalkylene glycol and a preformed copolymer of L-lactide and glycolide, wherein the weight ratio of polyalkylene glycol to preformed copolymer of L-lactide and glycolide employed in the copolymerization is from about 2:1 to about 1:2, respectively and wherein said preformed copolymer of L-lactide and glycolide consists essentially of from about 65-90 mole percent lactide and from about 10-35 mole percent glycolide.

15. The method of claim 14 wherein said suture is a synthetic, absorbable, multifilament suture.

16. The method of claim 15 wherein the synthetic absorbable, multifilament suture is comprised of homopolymers or copolymers of lactide and glycolide.

17. The method of claim 15 wherein said synthetic, absorbable, multifilament suture is a braided suture.

18. The method of claim 17 wherein the braided suture is filled with a water soluble hygroscopic polyhydroxy compound.

19. The method of claim 18 wherein said water soluble hygroscopic polyhydroxy compound is glycerin.

* * * * *

UNITED STATES PATENT AND TRADEMARK OFFICE
CERTIFICATE OF CORRECTION

PATENT NO. : 5,123,912
DATED : June 23, 1992
INVENTOR(S) : Donald S. Kaplan et al It is certified that error appears in the above-indentified patent and that said Letters Patent is hereby corrected as shown below:

| | |
|---|---|
| Column 3, line 5 | change "HO{RO}$_x$H" to -- HO{RO}$_y$H -- |
| Column 4 line 36 | after "application" insert -- (U.S. Serial No. 07/089,735) now U.S. Patent No. 5,037,429) -- |
| Column 5, line 59 | after "application" insert -- (U.S. Serial No. 07/089,735) now U.S. Patent No. 5,037,429) -- |
| Column 8, line 25 | change "abut" to -- about -- |
| Column 9, line 9 | change "abut" to -- about -- |
| Column 12, line 7 | change "HO{RO}$_x$H" to -- HO{RO}$_y$H |

Signed and Sealed this

Nineteenth Day of July, 1994

Attest:

BRUCE LEHMAN

*Attesting Officer*     *Commissioner of Patents and Trademarks*